(12) United States Patent
Rozhkova et al.

(10) Patent No.: US 10,220,378 B2
(45) Date of Patent: Mar. 5, 2019

(54) SEMICONDUCTOR-METAL NANOPARTICLE HYBRIDS WITH NATURAL AND ARTIFICIAL PROTON PUMP FOR HYDROGEN PRODUCTION

(71) Applicant: UCHICAGO ARGONNE, LLC, Chicago, IL (US)

(72) Inventors: Elena A. Rozhkova, Lemont, IL (US); Peng Wang, Shandong (CN); Richard D. Schaller, Clarendon Hills, IL (US); Nada M. Dimitrijevic, Lemont, IL (US); Tijana Rajh, Naperville, IL (US); Shankar G. Balasubramanian, Lemont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 15/611,674

(22) Filed: Jun. 1, 2017

(65) Prior Publication Data

US 2018/0345263 A1 Dec. 6, 2018

(51) Int. Cl.
*B01J 31/00* (2006.01)
*B01J 31/38* (2006.01)
(Continued)

(52) U.S. Cl.
CPC ............. *B01J 31/38* (2013.01); *B01J 21/063* (2013.01); *B01J 23/42* (2013.01); *B01J 31/062* (2013.01);
(Continued)

(58) Field of Classification Search
None
See application file for complete search history.

(56) References Cited

U.S. PATENT DOCUMENTS 6,524,997 B1 * 2/2003 Higo ................... B01J 35/002
502/350
7,351,563 B2 4/2008 Swartz et al.
(Continued)

FOREIGN PATENT DOCUMENTS

CN 104561152 A 4/2015
WO WO-2008/141230 A1 11/2008

OTHER PUBLICATIONS

Balasubramanian et al, High-Performance Bioassisted Nanophotocatalyst for Hydrogen Production, nanoletters, 13, pp. 3365-3371 (Year: 2013).*

(Continued)

*Primary Examiner* — Melvin C. Mayes
*Assistant Examiner* — Stefanie J Cohen
(74) *Attorney, Agent, or Firm* — Foley & Lardner LLP

(57) ABSTRACT

Aspects of the disclosure relate to an efficient entirely man-made nanobio hybrid fabricated through cell-free expression of transmembrane proton pump followed by assembly of the synthetic protein architecture with semiconductor nanoparticles for photocatalytic $H_2$ evolution. The system produces $H_2$ at a turnover rate of 240 μmol of $H_2$ (μmol protein)$^{-1}$ h$^{-1}$ under green and 17.74 mmol of $H_2$ (μmol protein)$^{-1}$ h$^{-1}$ under white light at ambient conditions, in water at neutral pH with methanol as a sacrificial electron donor. Robsutness and flexibility of this approach allows for systemic manipulation at nanoparticle-bio interface toward directed evolution of energy materials and devices.

15 Claims, 11 Drawing Sheets

(51) Int. Cl.
| | |
|---|---|
| C07K 17/14 | (2006.01) |
| B01J 23/42 | (2006.01) |
| B01J 21/06 | (2006.01) |
| B01J 31/06 | (2006.01) |
| B01J 35/00 | (2006.01) |
| B01J 37/02 | (2006.01) |
| C01B 3/04 | (2006.01) |
| H01M 8/0606 | (2016.01) |

(52) U.S. Cl.
CPC ......... *B01J 35/004* (2013.01); *B01J 35/0006* (2013.01); *B01J 35/0013* (2013.01); *B01J 37/0219* (2013.01); *B01J 37/0221* (2013.01); *B01J 37/0244* (2013.01); *C01B 3/042* (2013.01); *C07K 17/14* (2013.01); *H01M 8/0606* (2013.01); *B01J 2231/005* (2013.01); *B01J 2531/005* (2013.01)

(56) References Cited

U.S. PATENT DOCUMENTS

| 8,574,463 | B2 | 11/2013 | Tani et al. | |
|---|---|---|---|---|
| 8,865,441 | B2 | 10/2014 | Swartz et al. | |
| 9,133,486 | B2 | 9/2015 | Smith et al. | |
| 2010/0291189 | A1* | 11/2010 | Yokoyama | A61K 9/127 424/450 |
| 2011/0012096 | A1* | 1/2011 | Carmeli | B82Y 10/00 257/40 |
| 2016/0346763 | A1* | 12/2016 | Wahab | B01J 21/063 |

OTHER PUBLICATIONS

Rodriguez et al, From solar photocatalysis to fuel-cell: A hydrogen supply chain, journal of environmental chemical engineering 4, pp. 3001-3005 (Year: 2016).*
"MembraneMax Protein Expression Kits User Guide," Life Technologies, 52 pages (2012).
Allam, et al., "Bacteriorhodopsin/TiO2 nanotube arrays hybrid system for enhanced photoelectrochemical water splitting," Energy & Environmental Science 4, pp. 2909-2914 (2011).
Aono & Ariga, "The Way to Nanoarchitectonics and the Way of Nanoarchitectonics," Advanced Materials 28(6), pp. 989-992 (2016).
Ariga, et al., "Nanoarchitectonics for Dynamic Functional Materials from Atomic-/Molecular-Level Manipulation to Macroscopic Action," Advanced Materials 28(6), pp. 1251-1286 (2016).
Balasubramanian, et al., "High-Performance Bioassisted Nanophotocatalyst for Hydrogen Production," Nano Letters 13(7), pp. 3365-3371 (2013).
Bayburt, et al,. "Self-assembly of discoidal phospholipid bilayer nanoparticles with membrane scaffold proteins," Nano Letters 2(8), pp. 853-856 (2002).
Bora, et al., "Functionalization of Nanostructured Hematite Thin-Film Electrodes with the Light-Harvesting Membrane Protein C-Phycocyanin Yields an Enhanced Photocurrent," Advanced Functional Materials 22(3), pp. 490-502 (2012).
Denisov & Sligar, "Nanodiscs for structural and functional studies of membrane proteins," Nature Structural & Molecular Biology vol. 23, pp. 481-486 (2016).
Denisov, et al., "Directed Self-Assembly of Monodisperse Phospholipid Bilayer Nanodiscs with Controlled Size," Journal of the American Chemical Society 126(11), pp. 3477-3487 (2004).
Dominik & Kossiakoff, "Chapter Eleven—Phage Display Selections for Affinity Reagents to Membrane Proteins in Nanodiscs," Methods in Enzymology 557, pp. 219-245 (2015).
Dominik, et al,. "Conformational Chaperones for Structural Studies of Membrane Proteins Using Antibody Phage Display with Nanodiscs," Structure 24(2), pp. 300-309 (2016).
Evans, et al., "Enhanced Photocatalytic Hydrogen Evolution by Covalent Attachment of Plastocyanin to Photosystem I," Nano Letters 4(10), pp. 1815-1819 (2004).
Fujishima & Honda, "Electrochemical Photolysis of Water at a Semiconductor Electrode," Nature 238, pp. 37-38 (1972).
Gibson, et al., "Creation of a Bacterial Cell Controlled by a Chemically Synthesized Genome," Science 329(5987), pp. 52-56 (2010).
Grimme, et al., "Photosystem I/Molecular Wire/Metal Nanoparticle Bioconjugates for the Photocatalytic Production of H2," Journal of the American Chemical Society 130(20), pp. 6308-6309 (2008).
Hampp, "Bacteriorhodopsin as a photochromic retinal protein for optical memories," Chemical Reviews 100(5), pp. 1755-1776 (2000).
Herbst, et al., "Femtosecond infrared spectroscopy of bacteriorhodopsin chromophore isomerization," Science 297(5582), pp. 822-825 (2002).
Hodgman & Jewett, "Cell-free synthetic biology: Thinking outside the cell," Metabolic Engineering 14(3), pp. 261-269 (2012).
Iwuchukwu, et al., "Self-organized photosynthetic nanoparticle for cell-free hydrogen production," Nature Nanotechnology 5, pp. 73-79 (2010).
Jewett, et al., "An integrated cell-free metabolic platform for protein production and synthetic biology," Molecular Systems Biology 4, 220, 10 pages (2008).
Jin, et al., "Bacteriorhodopsin (bR) as an electronic conduction medium: Current transport through bR-containing monolayers," Proceedings of the National Academy of Sciences USA 103(23), pp. 8601-8606 (2006).
Johnson, et al., "The photocycle and ultrafast vibrational dynamics of bacteriorhodopsin in lipid nanodiscs," Physical Chemistry Chemical Physics 16, pp. 21310-21320 (2014).
Kalisman, et al., "Perfect Photon-to-Hydrogen Conversion Efficiency," Nano Letters 16(3), pp. 1776-1781 (2016).
Kandori, "Ion-pumping microbial rhodopsins," Frontiers in Molecular Biosciences 2(52), 11 pages (2015).
Karim & Jewett, "A cell-free framework for rapid biosynthetic pathway prototyping and enzyme discovery," Metabolic Engineering 36, pp. 116-126 (2016).
Kuai, et al., "Designer vaccine nanodiscs for personalized cancer immunotherapy," Nature Materials vol. 16, pp. 489-496 (2017).
Kuhlbrandt, "Bacteriorhodopsin—the movie," Nature 406, pp. 569-570 (2000).
Kuhlbrandt, "Structural biology: Chlorophylls galore," Nature 411, pp. 896-899 (2001).
Lewis, "Research opportunities to advance solar energy utilization," Science 351(6271),(2016).
Lewis, "Toward cost-effective solar energy use," Science 315(5813), pp. 798-801 (2007).
Li, et al., "Photovoltaic characteristics of BR/p-silicon heterostructures using surface photovoltage spectroscopy," Journal of Vacuum Science & Technology A 19, 1037 (2001).
Lyukmanova, et al., "Lipid-Protein Nanoscale Bilayers:? A Versatile Medium for NMR Investigations of Membrane Proteins and Membrane-Active Peptides," Journal of the American Chemical Society 130(7), pp. 2140-2141 (2008).
Maeda, "Photocatalytic water splitting using semiconductor particles: History and recent developments," Journal of Photochemistry and Photobiology C: Photochemistry Reviews 12(4), pp. 237-268 (2011).
Maeda, et al., "Photocatalyst releasing hydrogen from water," Nature 440, p. 295 (2006).
Mathies, et al,. "Direct Observation of the Femtosecond Excited-State Cis-Trans Isomerization in Bacteriorhodopsin," Science 240(4853), pp. 777-779 (1988).
Nabiev, et al.,"The Chromophore-Binding Site of Bacteriorhodopsin—Resonance Raman and Surface-Enhanced Resonance Raman-Spectroscopy and Quantum Chemical Study," Journal of Biosciences 8(1-2), pp. 363-374 (1985).
Nasr, et al,. "Covalently circularized nanodiscs for studying membrane proteins and viral entry," Nature Methods vol. 14, pp. 49-52 (2017).
Nassal, et al., "Structure-Function Studies on Bacteriorhodopsin .3. Total Synthesis of a Gene for Bacterioopsin and Its Expression in *Escherichia-coli*," Journal of Biological Chemistry 262, pp. 9264-9270 (1987).

(56) References Cited

OTHER PUBLICATIONS

Oesterhelt & Stoeckenius, "Functions of a new photoreceptor membrane," Proceedings of the National Academy of Sciences USA 70(10), pp. 2853-2857 (1973).
Oesterhelt & Stoeckenius, "Rhodopsin-like protein from the purple membrane of Halobacterium halobium," Nature New Biology 233, pp. 149-152 (1971).
Ohno, et al., "Morphology of a TiO2 Photocatalyst (Degussa, P-25) Consisting of Anatase and Rutile Crystalline Phases," Journal of Catalysis 203, pp. 82-86 (2001).
Rakovich, et al., "Resonance Energy Transfer Improves the Biological Function of Bacteriorhodopsin within a Hybrid Material Built from Purple Membranes and Semiconductor Quantum Dots," Nano Letters 10(7), pp. 2640-2648 (2010).
Reisner, et al., "Visible Light-Driven H2 Production by Hydrogenases Attached to Dye-Sensitized TiO2 Nanoparticles," Journal of the American Chemical Society 131(51), pp. 18457-18466 (2009).
Rosenblun & Cooperman, "Engine out of the chassis: Cell-free protein synthesis and its uses," FEBS Letters 588(2), pp. 261-268 (2014).
Roy, et al., "Spin-Controlled Photoluminescence in Hybrid Nanoarticles Purple Membrane System," ACS Nano 10(4), pp. 4525-4531 (2016).
Rozhkova & Wang, "Harnessing Nature's Purple Solar Panels for Photoenergy Conversion," World Scientific Series in Nanoscience and Nanotechnology vol. 12: Nanomaterials for Photocatalytic Chemistry, pp. 195-227 (2016).
Schenkl, et al., "Insights into excited-state and isomerization dynamics of bacteriorhodopsin from ultrafast transient UV absorption," Proceedings of the National Academy of Sciences USA 103(11), pp. 4101-4106 (2006).
Schrantz, et al., "Hematite photoanode co-functionalized with self-assembling melanin and C-phycocyanin for solar water splitting at neutral pH," Catalysis Today 284, pp. 44-51 (2017).
Shenkarev, et al., "Lipid-Protein Nanodiscs as Reference Medium in Detergent Screening for High-Resolution NMR Studies of Integral Membrane Proteins," Journal of the American Chemical Society 132(16), pp. 5628-5629 (2010).
Shih, et al., "Disassembly of Nanodiscs with Cholate," Nano Letters 7(6), pp. 1692-1696 (2007).
Stepien, et al., "Comparative EPR studies on lipid bilayer properties in nanodiscs and liposomes," BBA—Biomembranes 1848(1)(A), pp. 60-66 (2015).
Sullivan, et al., "A cell-free expression and purification process for rapid production of protein biologics," Biotechnical Journal 11(2), pp. 238-248 (2016).
Timm, et al., "Toward Microfluidic Reactors for Cell-Free Protein Synthesis at the Point-of-Care," Small 12(6), pp. 810-817 (2016).
Utschig, et al., "Photocatalytic Hydrogen Production from Noncovalent Biohybrid Photosystem I/Pt Nanoparticle Complexes," Journal of Physical Chemistry Letters 2(3), pp. 236-241 (2011).
Van Eps, et al., "Characterizing rhodopsin signaling by EPR spectroscopy: from structure to dynamics," Photochemical & Photobiological Sciences 14, pp. 1586-1597 (2015).
Voloshin & Swartz, "Efficient and scalable method for scaling up cell free protein synthesis in batch mode," Biotechnology and Bioengineering 91(4), pp. 516-521 (2005).
Voloshin & Swartz, "Large-Scale Batch Reactions for Cell-Free Protein Synthesis," Cell-Free Protein Synthesis: Methods and Protocols, pp. 207-236 (2008).
Wagner, et al., "Directed evolution of bacteriorhodopsin for applications in bioelectronics," Journal of the Royal Society Interface 10(84), 15 pages (2013).
Wang, et al., "Photoinduced Electron Transfer Pathways in Hydrogen-Evolving Reduced Graphene Oxide-Boosted Hybrid Nano-Bio Catalyst," ACS Nano 8(8), pp. 7995-8002 (2014).
Yoon, et al., "Visible light photocatalysis as a greener approach to photochemical synthesis," Nature Chemistry 2, pp. 527-532 (2010).
Zhao, et al., "Bacteriorhodopsin/Ag nanoparticle-based hybrid nanobio electrocatalyst for efficient and robust H2 evolution from water," Journal of the American Chemical Society 137(8), pp. 2840-2843 (2015).

\* cited by examiner

FIGURE 1A
FIGURE 1B
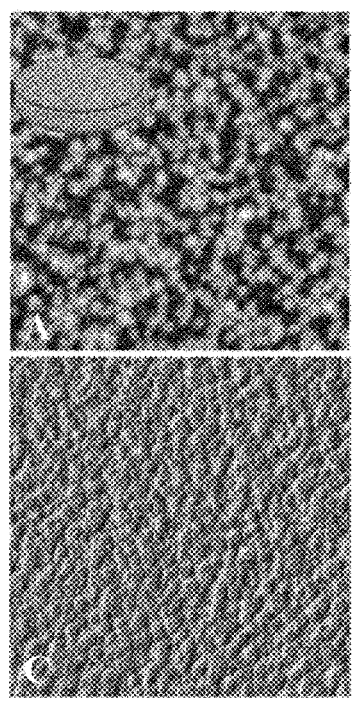
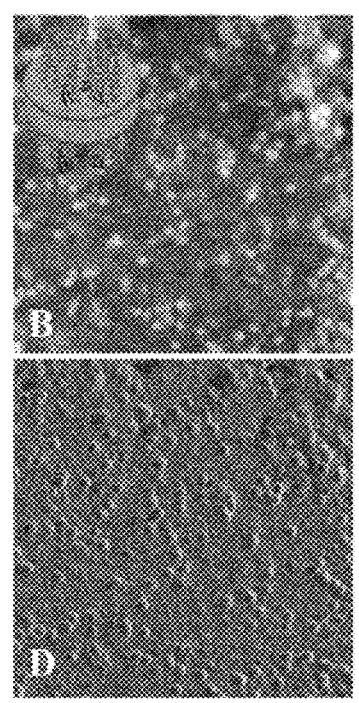
FIGURE 1C
FIGURE 1D

SEMICONDUCTOR-METAL NANOPARTICLE HYBRIDS WITH NATURAL AND ARTIFICIAL PROTON PUMP FOR HYDROGEN PRODUCTION

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

TECHNICAL FIELD

The present disclosure relates generally to hybrid photocatalysts comprised of semiconductor nanoparticles and biological materials.

BACKGROUND

The newest Anthropocene epoch is characterized by two interrelated human activity-associated phenomena—exhaustion of natural resources along with strong environmental footprint from one side and vigorous development of cutting-edge technologies such as nanotechnology, artificial photosynthesis and synthetic biology from the other side. To address global energy challenges it is necessary to develop efficient yet environmentally-friendly energy sources as an alternative to hydrocarbons feedstocks. Biologically-inspired photocatalytic transformation of solar energy and water to clean fuels such as hydrogen using semiconductors is among the most promising dynamically evolving renewable energy technologies. "Greener" schemes of photocatalytic visible-light hydrogen production along with inorganic material utilize biological structures capable of water splitting, light-harvesting or proton reduction. Applicants have been developing visible light-driven nanobio photocatalysts for hydrogen production based on non-covalent assemblies of the natural membrane proton pump bacteriorhodopsin bR and $TiO_2$ semiconductor nanoparticles. While in a natural environment the neat protein machinery of the bR proton pump carries sunlight-driven transmembrane proton transfer providing an electrochemical gradient for synthesis of ATP, in engineered water splitting systems in addition to preserved inherent function it also acts as a visible light photosynthesizer that injects photoexcited electrons into the conduction band of a semiconductor.

With the advent of modern life science technologies, or "synthetic life", it became achievable to design and produce key functional components of life, including chemically synthesized DNA circuits, proteins and artificial cell membranes from scratch. For example, a living bacteria can be re-programmed via transplantation of chemically-synthesized genome for rebooting cell with new desired function such as biosyntheses of fine chemicals, protein therapeutics or renewable biofuels. On the other hand, it also became achievable to accomplish one of the core cellular function, protein biosynthesis, outside of a living cell confined space, or "cell-free," through assembly of key logic elements of a cell, namely artificial biomembrane as a template, synthetic DNA as a blueprint, an isolated biological translation machinery of ribosome along with supply of energy-rich chemicals, aminoacids, cofactors and enzymes. Cell-free protein synthesis is a powerful flexible bottom-up approach that while utilizing minimum of cellular elements allows for labor- and time-efficient protein expression in a test tube without multistep complex maintenance of a living culture. Membrane proteins and cell machineries whose functions critically depend on interface with lipid bilayer environment, e.g. G-protein-coupled receptor, cytochrome P450 oxygenases and rhodopsins, have been expressed cell-free in soluble function-preserved form as supramolecular complexes using the nanodiscs artificial membrane detergent-free technology. The nanodiscs represent lipid bilayer nanoparticles (FIG. 4) with controllable dimensions which self-assemble with helical protein "belts" (membrane scaffold protein, assigned as 1E3D1). Dimensions and high degree of homogeneity of the nanodiscs are securely controlled by the length of the scaffold protein. Thus far, the cell-free nanodiscs approach has been mainly applied for structural biology (including NMR, EPR, X-ray and neutron scattering protein characterization), peptide- and protein-membrane interactions studies and single molecule measurements. Other applications include phage-display drug development, microfluidic on-demand point-of-care therapeutic protein expression and designer vaccine for cancer immunotherapy.

SUMMARY

Applicants demonstrate that a minimalistic cell-free strategy for production of artificial transmembrane protein complexes can be employed as chassis for construction of functional bionanocatalytic heterostructures and devices capable of photon energy-to-hydrogen transformation. The examples disclose supramolecular complexes of bacteriorhodospin proton pump cell-free expressed in artificial membranes were directly assembled with $Pt/TiO_2$ nanophotocatalyst for visible light-driven hydrogen production at ambient conditions.

Aspects of the disclosure relate to a nano-bio hybrid material comprising a biological component, a proton pump, and a semiconductor component. In some embodiments, these components are non-covalently coupled. Further aspects relate to the use of this nano-bio hybrid material as a photocatalyst. In some embodiments, the photocatalyst is active in white light and/or neutral pH in a presence of a sacrificial electron donor. Still further aspects relate to the use of this photocatalyst in a fuel cell or in a method of generating hydrogen by photocatalytic water splitting. In some embodiments relating to fuel cells, the photocatalyst may be provided as an aqueous slurry.

In some embodiments, the proton pump is synthetically produced. In some embodiments, this synthetic production is achieved through use of a cell-free system. In some embodiments, the proton pump is an opsin. Non-limiting exemplary opsins for use herein include: microbial bacteriorhodopsin from Archaea, proteorhodopsin from proteobacetria and *Fulvimarina pelagi*, rhodopsin from marine bacetria, halorhodopsin from Archaea, those described in Kandori, H. Ion-pumping microbial rhodopsins. *Frontiers Mol. Biosci.* 2(52):1-11 (2015), and similar rhodopsins, including animal rhodopsins, capable of the light-driven translocation of ions across the membrane. As disclosed herein, the opsins may be wild type or engineered mutants, isolated from natural sources, expressed in host cells or expressed in cell-free systems. In some embodiments, the opsin is bacterial rhodopsin.

In some embodiments, the semiconductor component comprises a metal oxide. Non-limiting examples of metal oxides for use herein include: Si, SiC, GaAs, GaInP, GaN, CdS, CdSe, $TiO_2$, $VO_2$, $ZrO_2$, $Fe_3O_4$, $Fe_2O_3$, $MnO_2$, NiO, ZnO, $Bi_2O_3$ and CuO. In some embodiments the metal oxide is $TiO_2$. In some embodiments, the semiconductor component may further comprise a co-catalyst. Non-limiting examples of co-catalysts for use herein include Pt, Pd, Au, Ag, and composites of thereof. In some embodiments, the co-catalyst is Pt. In some embodiments, the semiconductor component further comprises one or more of a typical IV semiconductor, an III-V semiconductor and a II-VI compound semiconductor. Non-limiting examples of typical semiconductors contemplated herein include those listed at en.wikipedia.org/wiki/List_of_semiconductor_materials or GaAs, described in detail in Kang et al. (2017) *Nature Energy* 43:17043.

In some embodiments, the semiconductor component is a nanocluster or other nano-structure comprised of the metal oxide. In further embodiments, the co-catalyst may be dotted on the nanocluster or other nano-structure.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIGS. 1A-1D show 1×1 μkm AFM amplitude and phase images of the lipoprotein disks before (A, C) and after (B, D) expression of the bRsyn.

Figure 1E:
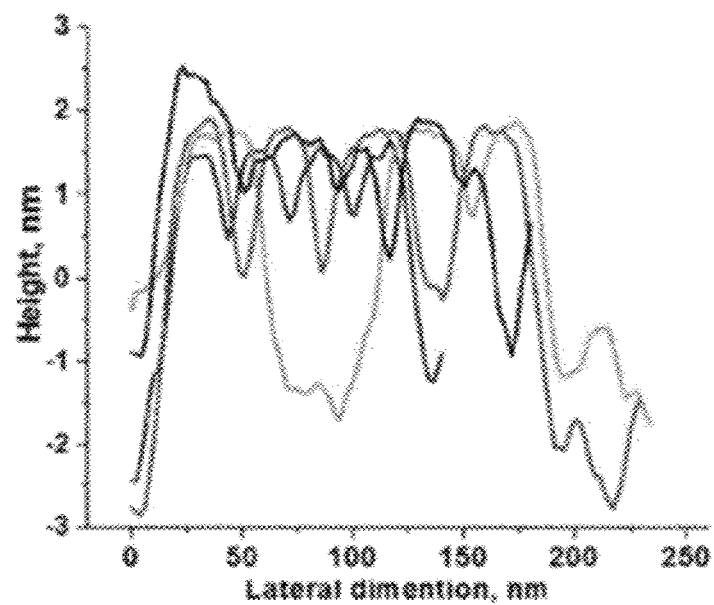
FIGS. 1E-1F show topography cross-section (1E: before- and 1F: after)-transmembrane protein expression.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

The present disclosure relates to the use of in vitro cell-free expressed membrane proton pump for construction of nano-bio hybrid material for nanobiocatalytic photon-to-hydrogen transformation.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The components disclosed herein can take a variety of forms. Aspects of the disclosure relate to nano-structures (between 0.1 and 100 nm) termed "nano-bio hybrids." Nano-structures relevant to the disclosure include but are not limited to nanoparticles, nanodiscs, nanoclusters, nanofibers, nanowires, nanosheets, nanopillars, nanoribbons, quantum dots, nanofilms and single-layer foils. Nanoclusters, for example, are clusters of nanoparticles, generally having a narrow size distribution, optionally ranging between about 1 nm to about 10 nm. Nano-bio structures can include biological structures integrated with nanoparticles through chemical bond or via physisorption. The nanobio hybrid can be slurry, 2D-dimensional or (films, arrays) or 3D-dimensional assemblies and frameworks (core-shell structures comprised of plurality of nanoparticles fused with biological structures such as vesicles, emulsions, capsules, droplets).

The term "photocatalyst" as used herein refers to a substance that drives a light-catalyzed reaction.

As used herein, "synthetically produced" when used in context of a protein intends the artificial production of a protein, i.e. not naturally made. Examples of synthetic production include, but are not limited to, recombinant expression and generation of proteins in cell-based systems or in a cell-free system. The term "cell-free" is defined hereinabove.

The term "proton pump" as used herein refers to a membrane protein (typically a transmembrane protein) capable of transporting protons across a biological membrane. One example of a proton pump is an opsin. Opsins are a group of light-sensitive proteins that convert a photo of light into an electrochemical signal. Non-limiting examples of opsins include microbial bacteriorhodopsin from Archaea, proteorhodopsin from proteobacetria and *Fulvimarina pelagi* rhodopsin from marine bacetria, halorhodopsin from Archaea, those described in Kandori, H. Ion-pumping microbial rhodopsins. *Frontiers Mol. Biosci.* 2(52):1-11 (2015), and similar rhodopsins, including animal rhodopsins, capable of the light-driven translocation of ions across the membrane, as well as their protein-engineered mutants. Bacteriorhodopsin is an exemplary opsin found in archaea bacteria that acts as a proton pump. A non-limiting exemplary sequence for bacteriorhodopsin is the sequence associated with GenBank Accession No. J02755, noted below:

MQAQITGRPEWIWLALGTALMGLGTLYFLVKGMGVSDPDAKKFYAITTLV

PAIAFTMYLSMLLGYGLTMVPFGGEQNPIYWARYADWLFTTPLLLLDLAL

LVDADQGTILALVGADGIMIGTGLVGALTKVYSYRFVWWAISTAAMLYIL

YVLFFGFTSKAESMRPEVASTFKVLRNVTVVLWSAYPVVWLIGSEGAGIV

PLNIETLLFMVLDVSAKVGFGLILLRSRAIFGEAEAPEPSAGDGAAATS

Homologs of bacteriorhodopsin include halorhodopsin and channelrhodopsin. Natural sources for bacteriorhodopsin include bacteria from the genus *Halobacterium*, proteorhodopsin—proteobacteria. Synthetically produced bacteriorhodopsin may be generated using the cell-free system described herein.

The terms "coupled," "connected," "integrated" and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

As used herein, the term "non-covalently" refers to the coupling of two or more molecules that is not characterized by the formation of a covalent bond. Non-limiting examples of non-covalent interactions include ionic bonding, hydrogen bonding, halogen bonding, Van der Waals forces, dipole-dipole, dipole-induced dipole, London dispersion forces, π-effects, and hydrophobic effects.

The term "semiconductor" is known in the art to refer to any material that acts as an insulator at low temperatures but has appreciable electrical conductivity, resembling a metal, at high temperatures. Metal oxides, for example, are known in the art to be functional semiconductors. Non-limiting examples of such metal oxides include Si, SiC, GaAs, GaInP, GaN, CdS, CdSe, $TiO_2$, $VO_2$, $ZrO_2$, $Fe_3O_4$, $Fe_2O_3$, $MnO_2$, NiO, ZnO, $Bi_2O_3$ and CuO. Other semiconductors include a typical IV semiconductor, an III-V semiconductor and a II-VI compound semiconductor. Semiconductors may be doped with co-catalysts to alter their conductivity. For example, where the semiconductor is nano-scale, nanoparticles of the co-catalyst may be dotted on the nano-structure. Non-limiting examples of co-catalysts include Pt, Pd, Au, Ag, and composites of thereof.

As used herein, the term "white light" refers to the range of wavelengths from about 350 nm≤λ≤about 800 nm, applied at an intensity of about 120 mW/cm$^2$.

As used herein, the term "neutral pH" refers to a pH value that is neither acidic nor basic, i.e. about 7.0.

The term "fuel cell" refers to any device that converts energy into fuel. In some embodiments, the energy converted is energy of light into chemical and the conversion to fuel occurs through the photocatalytic water splitting reaction. Fuel cell configurations are known in the art and are disclosed in a variety of references including. Fuel cells may be used in a variety of applications to generate energy. The minimal basic elements include a vessel with glass or/and quartz window and gas inlet and outlet.

The term "photocatalytic water splitting" and variations thereof is used to describe the technique for hydrogen generation, known in the art, involving the dissociation of water into its constituent parts ($H_2$ and $O_2$) through photocatalysis. Photocatayltic water splitting may be useful in a variety of energy generating fields, e.g. the hydrogen produced by photocatalytic water splitting may be used in a traditional fuel cell which burns hydrogen fuel to yield water. For example, weather probes requiring energy may rely on hydrogen fuel obtained through such activity.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Exemplary Modes of Carrying Out the Disclosure

Embodiments described herein relate generally to nano-bio hybrids as hydrogen evolution reaction white-light photocatalysts. Such hybrids are produced through assembly of semiconductor nanoparticles (e.g. $TiO_2$), reduced graphene oxide (rGO), Pt metal nanoparticles with proton pump structures. The inorganic part is produced via photoreduction of precursors, while biological material can be either isolated from natural source, e.g. *Halobacteria* organisms, or synthetically produced, e.g. via cell-free expression.

In exemplary embodiments, P25 titanium dioxide $TiO_2$ is used as a semiconductor. Other nanocrystalline metal oxides, such as but not limited to: $VO_2$, $ZrO_2$, $Fe_3O_4$, $Fe_2O_3$, $MnO_2$, NiO and CuO. Metal co-catalysts nanoparticles, such as but not limited to: Pt, Pd, Au, Ag, and composites of thereof may also be used. The nano-bio hybrids catalyze hydrogen evolution reaction (HER) under white light exposure at neutral pH in presence of sacrificial e-donors and can be utilized either in photochemical reaction or as a photoelectrode material.

A further method of use involves using the bR membrane protein directly after sucrose gradient separation. Not to be bound by theory, Applicant believes that the presence of sucrose might be useful for two purposes: (1) freezing temperature of the aqueous catalytic slurry can be decreased that allows for applying our invention at high altitudes and (2) sugar can serve as an additional and/or sacrificial electron donor in the HER that addresses a problem of substituting methanol to less toxic and lower cost biomass-related substrates. Cheaper and environmentally friendly sacrificial reagents can include glycerol, a main side-component of biodiesel production waste, lignin, cellulose. Further, industrial processes water can be used, including saline chilling waters recycling, salt manufacturing from brines in natural or eco-friendly artificial pans.

Not to be bound by theory, Applicant believes the present disclosure is applicable to a variety of industries, including but not limited to the design of green environmentally friendly photocatalysts for energy (e.g. hydrogen as fuel and hydrogen gas for atmospheric probing using balloons, drones) as well as linking advanced vigorous research fields—nano- and materials chemistry, photocatalysis, synthetic biology, and artificial life systems.

EXAMPLES

The following examples are non-limiting and illustrative of procedures which can be used in various instances in carrying the disclosure into effect. Additionally, all reference disclosed herein below are incorporated by reference in their entirety.

Materials and Methods:

All trans-retinal and solvents were from Sigma. Highly dispersed Aeroxide $TiO_2$ P-25 (Evonik Industries) containing anatase and rutile crystalline phases in 80/20 ratio with a surface area of ~55 $m^2g^{-1}$ was used as a main framework. Sodium hexachloroplatinate, ethanol, methanol, hydrochloric acid, sodium sulfate, acetone, iodine were obtained from Sigma-Aldrich. Deionized (DI) ultrapure water (18 $M\Omega \cdot cm^{-1}$) was used for solution preparation. The His-Pur Ni-NTA agarose resin was purchased from the Thermo Scientific and used as directed by the manufacturer's imidazole gradient protocol for the poly-histidine-tagged protein purification via nickel affinity chromatography.

bRsyn (Artificial Purple Membranes) Cell-Free Expression and Purification.

Figure 6:
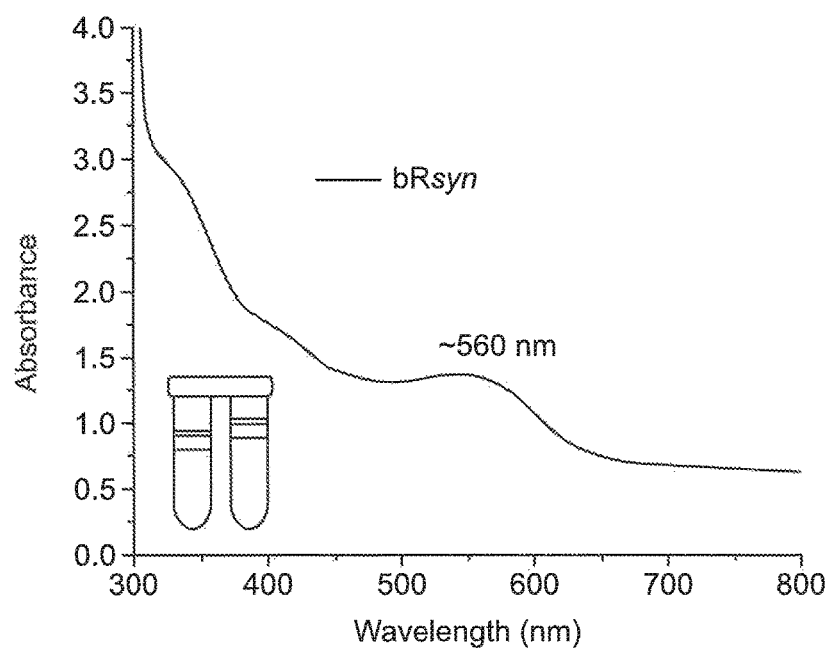
FIG. 6 depicts the UV-Vis spectrum of bRsyn; and two solutions of free all-trans retinal (yellow) and the synthetic protein reaction mixture resulting in bRsyn (pink-purple). Appearance of the characteristic absorption peak at ~560 nm indicates formation of a properly folded, functional proton bR containing retinal chromophore which covalently binds to the Lys 216 via a protonated Schiff base.

MembraneMax HN module, Invitrogen Life Technologies, (with the nanolipoprotein particles assembled from 1,2-dimyristoyl-sn-glycero-3-phosphocholine and polyhistidine-tagged membrane scaffold protein 1E3D1, Sigma-Aldrich) and the 3435 bp pEXP5-CT/bR expression vector, containing synthetic bR construct (GenBank Accession No. J02755) that allows the expression of the *Halobacterium salinarium* bR were from the Life Technologies. The cell-free expression was carried out in accordance with the manufacturer's protocol allowing for ~1 ml reaction mixture within around two and half hours, see Supplemental material references The Ni-NTA agarose resin was used as directed by the manufacturer's imidazole gradient protocol. Resulting bright pink colored product, lipoprotein nanodiscs-bRsyn complex, was suspended in 100 mM HEPES (pH 7.5) and stored at +4° C. Concentration of properly folded protein containing retinal cofactor covalently linked to Lys-216 via Schiff-base was determined spectrophotometrically using characteristic absorbance at 568 nm, molar extinction coefficient 62,700 $M^{-1}cm^{-1}$ as shown in FIG. 6.

Nano-Bio Photocatalyst Preparation.

Platinum nanoparticles were grown on $TiO_2$ P25 via photodeposition method reported before. The final $Pt/TiO_2$ photocatalyst was stored in DI water before use. The typical Pt loading was 0.5 wt % as determined by inductively coupled plasma atomic emission spectroscopy analyses. DI water solution of the bRsyn (0.5 nmol) cell-free expressed within in artificial lipoprotein discs was added to the 0.5 mL of the Pt/TiO$_2$ (3 mg/mL) photocatalyst particles slurry and agitated overnight to enable maximum absorption of the synthetic biomolecular architectures on the particles surface.

Hydrogen Evolution Measurements

The freshly prepared bRsyn-modified Pt/TiO$_2$ nanoparticles were transferred to 1 mL water/methanol (4:1 volume) solution reaction vessel sealed tightly with a rubber septum. The mixture was degassed with high-purity N$_2$ for 30 minutes. High pressure Xe lamp (200 W) equipped with a 10-cm IR water filter and a λ=560±10 nm band pass filter ( ) or λ>440 nm cut-off filter was used as the light source. Green light intensity of 13 mW/cm$^2$ and white light intensity of 120 mW/cm$^2$ were determined by light intensity meter (NOVAII laser power/energy monitor). The amount of photo-generated H$_2$ was detected and quantified with Agilent 7890A gas chromatograph (GC) equipped with a thermal conductivity detector (TCD) and HP PLOT Molesieve 5 A column which was held isothermally at 40° C. Pure N$_2$ (99.999%+) was used as a carrier gas at a flow rate of 3.5 mL min$^{-1}$. At the interval time, 20 μL aliquots of the gas sample from the headspace of the reaction vessel were collected and analyzed by the GC system.

Preparation of Photoelectrodes and Photoelectrochemical Measurements

TiO$_2$ and TiO$_2$-bRsyn photoelectrodes were prepared by electrophoretic deposition on an FTO electrode (area 1 cm$^2$) using Ti sheets as a counter electrode. The typical electrophoretic deposition was performed in acetone solution (50 mL) containing TiO$_2$ or TiO$_2$-rGO particles (50 mg) and iodine (10 mg). FTO and Ti sheets were dipped into the solution 1 cm apart and then 120 V bias was applied between them for 1 min using a potentiostat (Agilent E3612A). The film was then sintered at 250° C. in Ar gas for 20 min. The obtained TiO$_2$ electrode was modified with bRsyn (0.4 nmol) through overnight immersing in the dark and then rinsed with DI water before measurement.

The photoelectrochemical properties were investigated by a three-electrode system with TiO$_2$ or TiO$_2$-bRsyn as working electrodes, saturated Ag/AgCl as a reference electrode, and platinum wire as a counter electrode. The 0.1 M Na$_2$SO$_4$ at pH 6.5 electrolyte, was purged with pure N$_2$ (99.999%+) for 30 minutes before measurement to remove dissolved oxygen. High pressure Xe lamp (200 W) equipped with a 10-cm IR water filter and a band pass filter (560±10 nm) was used as the light source. Transient photo-current curves of different photoelectrodes were carried out at potentiostatic conditions (500 mV vs. Ag/AgCl electrode) under green light irradiation with power set to 13 mW/cm$^2$.

Transient Absorption Measurements

Transient absorption measurements were performed using a 2 kHz, 35 fs amplified titanium:sapphire laser. A portion of the 800-nm laser fundamental was mechanically delayed and focused into a sapphire plate to produce a broad-band white light probe. Pump pulses at 450 nm (fluence 75 μJ/cm$^2$) were produced using an optical parametric amplifier. Samples were measured under ambient conditions.

Atomic force microscopy surface images of the "empty" lipoprotein and bR-expressed nanodiscs absorbed on freshly cleaved mica (1×1 μm) were acquired in non-contact (tapping) mode using Atomic Microscope (Veeco Dimension 3100) with high resolution ultra-sharp TESP-SS AFM probe (Bruker).

Results and Discussion

Figure 1F:
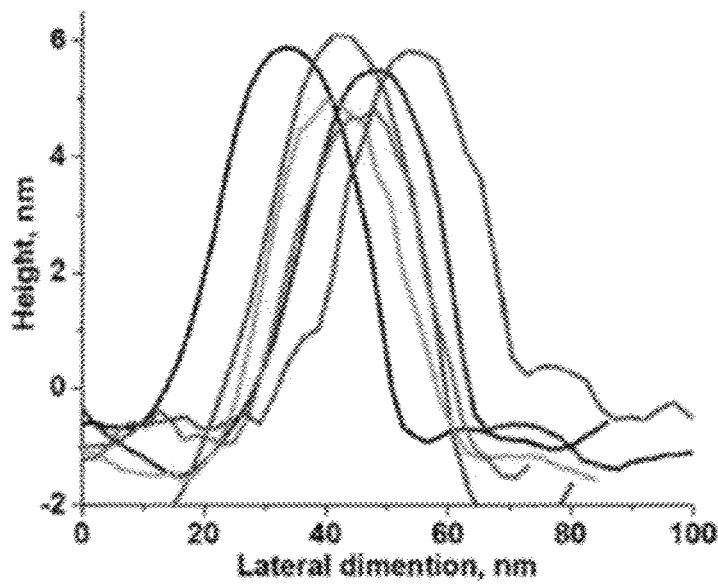

Synthetic purple membranes (PMsyn) were successfully cell-free expressed using the nanodiscs artificial lipoprotein membrane template and a vector containing synthetic DNA construct encoding bR. High-resolution Atomic Force Microscopy (AFM) images of the lipoprotein nanoparticles before and after the bRsyn expression reveals discrete nearly-monodisperse disc-shaped structures, as shown in FIGS. 1A-1D. While dimensions of the "bare" lipoprotein discs were detected to reach near ~20 nm in width and ~3.5 nm in height (FIG. 1A, and FIG. 1E), packing of the discs with expressed transmembrane bRsyn leads to noticeable sharpening and rounding of the discs topography (phase images in FIGS. 1C-1D) as well as narrowing of the diameter down to ~10 nm with simultaneous stretching of height up to ~7±0.5 nm (FIG. 1B, and FIG. 1F). This is in agreement with lateral dimension of 2-D lattice of the natural crystalline PM patches where retinal chromophore, the key element responsible for light-driven proton translocation, is positioned in the center of the PM at distance of around 2.5 nm from each side.

Figure 2:
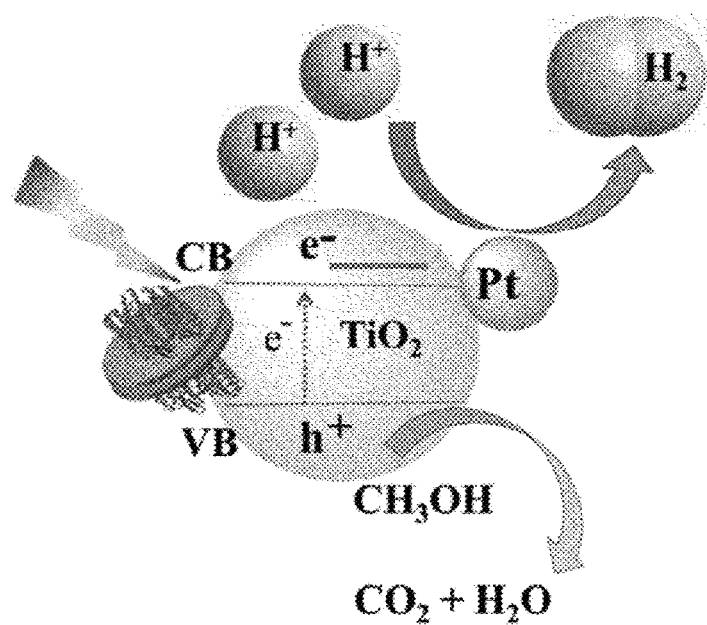
FIG. 2 is a depiction of the photocatalytic cycle over the entirely synthetic Pt/TiO$_2$-bRsyn hybrid nano-biocatalyst
Figure 10:
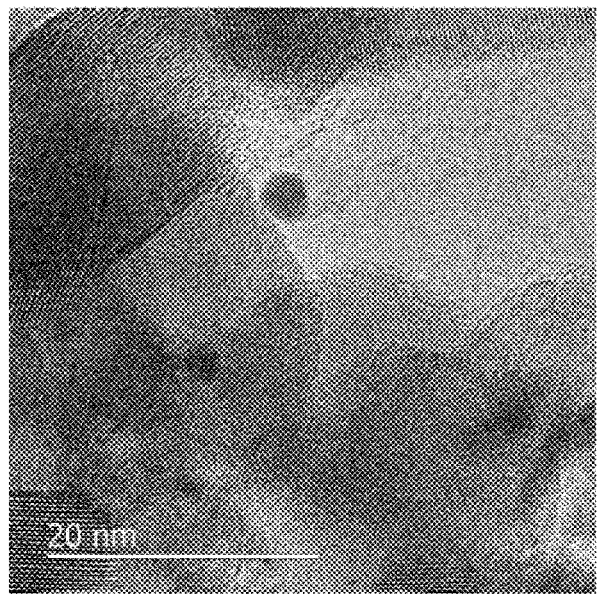
FIG. 10 depicts a HRTEM image of Pt co-catalyst nanoparticles photo-deposited on TiO$_2$.

After purification through nickel affinity chromatography the cell-free expressed proton pumps bRsyn (λ max 560 nm) (FIG. 6) were non-covalently assembled on the surface of semiconductor TiO$_2$ nanoclusters decorated with ~3 nm Pt co-catalyst dots (FIG. 10) resulting in entirely synthetic nanobio hybrid Pt/TiO$_2$-bRsyn, as schematically drawn in FIG. 2.

The photocatalytic performance of the synthetic Pt/TiO$_2$-bRsyn nanobio architecture toward hydrogen evolution from water was examined at neutral pH under either green or white light in the presence of methanol as a sacrificial electron donor, as schematized in FIGS. 1E-1F. As summarized in Table 1, when the nano-bio catalyst was exposed to monochromatic green light (λ 560±10 nm, absorbance maximum of properly folded wild type bR), at 13 mW/cm$^2$ a turnover rate of 240 μmol of H$_2$ (μmol protein)$^{-1}$ h$^{-1}$ of H$_2$ was detected. Under higher power 120 mW/cm$^2$ white light (λ 350-800 nm) the turnover rate increased by ~74 times reaching 17.74 mmol of H$_2$ (μmol protein)$^{-1}$ h$^{-1}$. In this way the synthetic cell-free expressed proton pump-based photocatalyst performed comparably or even better than previously reported nano-bio systems based on bR from *Halobacterium salinarum*.

The table below shows photocatalytic H$_2$ evolution by bR- and bRsyn-based nanobio assemblies in the presence of methanol as electron donor at pH 7.0 (a) under monochromatic green and white light illumination:

| | Rate of H$_2$ [μmole H$_2$ (mg protein)$^{-1}$ h$^{-1}$] | | |
| --- | --- | --- | --- |
| System | λ 560 ± 10 nm (13 mW/cm$^2$) | 350 ≤ λ ≤ 800 nm (120 mW/cm$^2$) | Reference |
| Pt/TiO$_2$-bR | 207 | 5275 | Balasubramanian et al[9] |
| Pt/TiO$_2$/rGO-bR | 298 | 11240 | Wang et al[10] |
| Pt/TiO$_2$-bRsyn | 240 | 17740 | This work |

Figure 7:
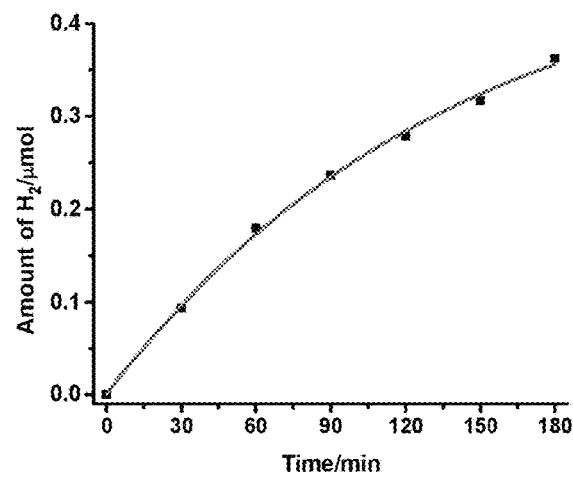
FIG. 7 shows photocatalytic H$_2$ evolution in the presence of methanol as electron donor at pH 7.0 under monochromatic green light, 560±10 nm (13 mW/cm$^2$), top, and under white light illumination (350 nm≤λ≤800 nm, 120 mW/cm$^2$), bottom.
Figure 7:
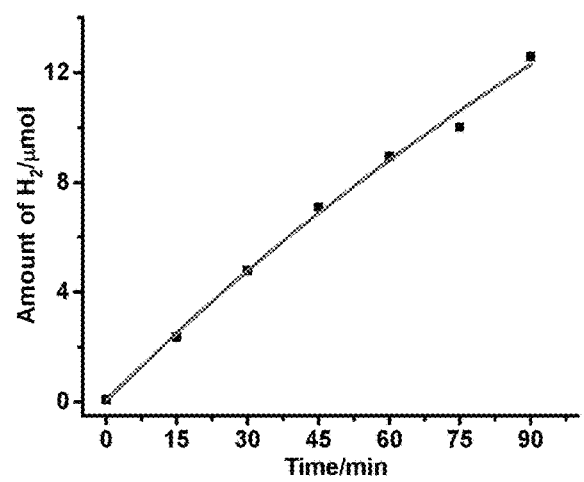

Notably, as compared to previous reports where natural PM patches were used in Applicants have found remarkably lower concentrations of the properly folded bRsyn protein were sufficient for the photocatalytic hydrogen evolution. Not to be bound by theory, this effect could be credited to monodispersity and better water dispensability of the synthetic supramolecular complexes and capability of discrete "discs" to more evenly interface with the semiconductor particles surface thus allowing more catalytic sites for interaction with water molecules as compared with natural PM patches. On average, nearly constant H$_2$ evolution under light illumination over the photocatalyst was observed for at least two-three hours, under green and white light, FIG. 7.

Figure 3:
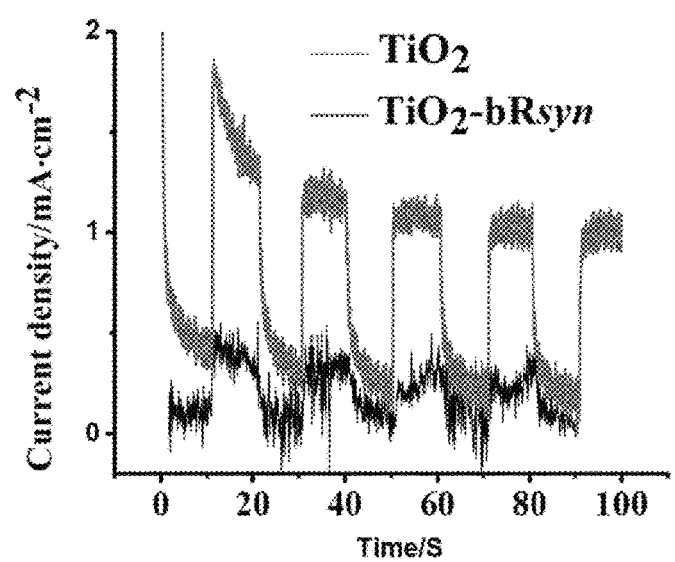
FIG. 3 shows photocurrent transient responses under green light irradiation. The green light density is 13 mW/cm$^2$; the electrolyte is 0.1 M aqueous Na$_2$SO$_4$, pH 6.5.
Figure 8:
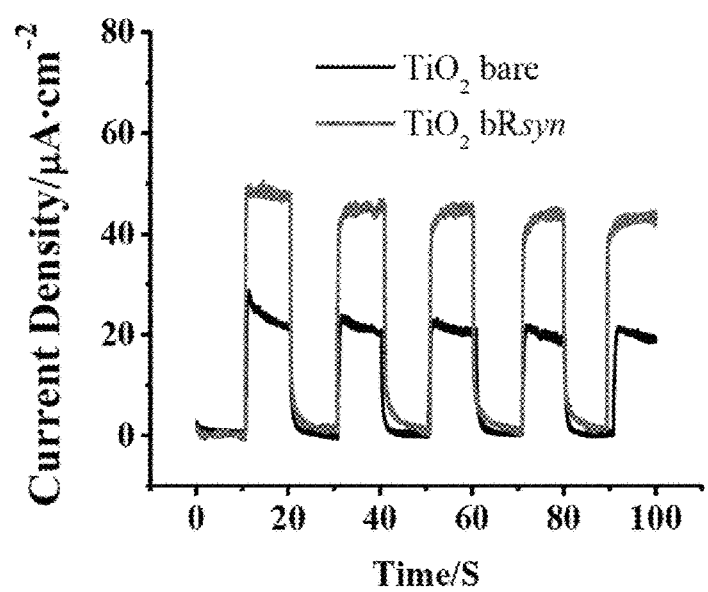
FIG. 8 shows photocurrent transient responses under white light irradiation. (350 nm≤λ≤800 nm, 120 mW/cm$^2$) The electrolyte is 0.1 M aqueous Na$_2$SO$_4$, pH 6.5.
Figure 9:
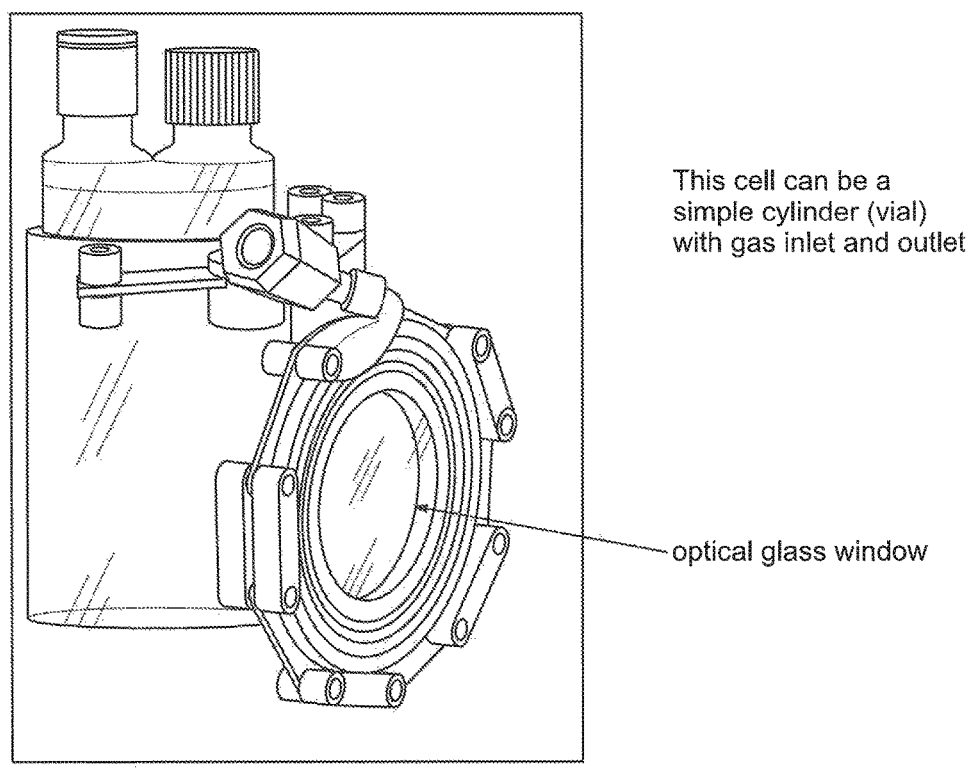
FIG. 9 is an exemplary schematic of a fuel cell configured for photocatalytic water splitting with the photocatalyst described herein.

To demonstrate the role of the synthetic biological architecture bRsyn in the photocatalytic activity photoelectrochemical measurements were carried out using the typical three-electrode system in 0.1 M $Na_2SO_4$ electrolyte (pH 6.5). $TiO_2$ particles were electrophoretically deposited on FTO conducting glass electrode as uniform film and then immersed in the bRsyn water solution allowing the biostructure to assemble on the nanoparticles surface. FIG. 3 shows that under present conditions in the dark bRsyn-functionalized photoelectrode shows negligible current response, while under monochromatic light irradiation, at 560±10 nm (10 $mW/cm^2$) the photocurrent increases rapidly reaching a steady-state current density of 1.5 $\mu A/cm^2$. After the light was turned off the photocurrent returned to the original background level, and the process could be repeated several times. As one might expect, the bare $TiO_2$ electrode with no bRsyn assembled did not show a detectable change in current under the monochromatic green light irradiation. This demonstrates that the origin of the photocurrent under the green light should be credited to the excitation of retinal chromophore in the synthetic supramolecular chromophore complex and charge transfer to the $TiO_2$ electrode. Consistent photocurrent transient responses under white light (light density 120 $mW/cm^2$) were also observed, FIG. 8.

Figure 4:
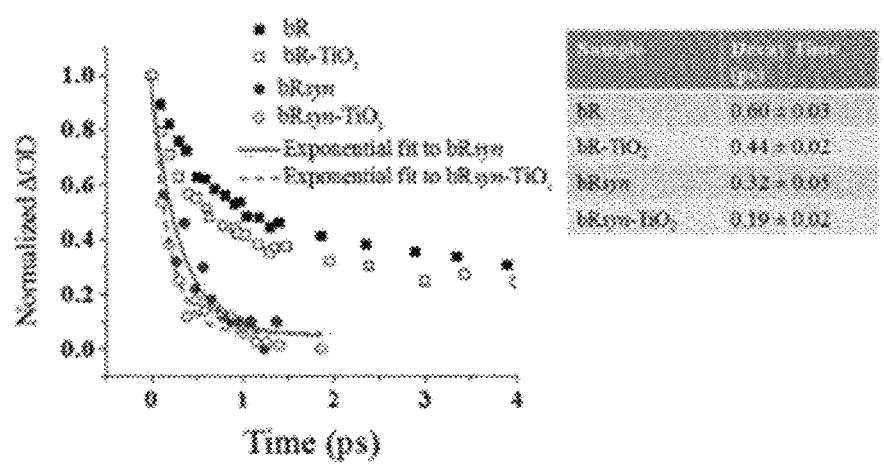
FIG. 4 depicts ultrafast transient absorption measurements showing the lifetime decay of the excited bR species reveal charge transfer from bR molecules to TiO$_2$ particles (25 μg/ml). The samples were pumped using 560 nm and probed at 625 nm laser pulses. Kinetic traces at 625 nm of bR and bR-TiO$_2$ samples along with exponential fit. Pump power: 907 μJ/cm$^2$ (2 mW).
Figure 5:
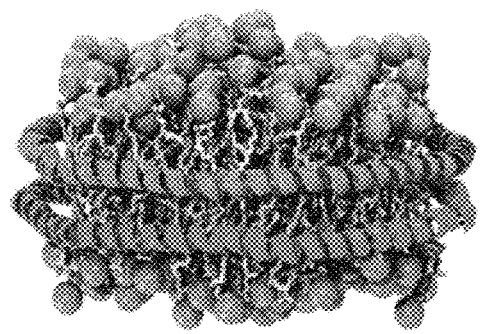
FIG. 5 is a schematic representation of a nanodisc (the lipid headgroups shown in orange, and the lipid tails in light tan), included with permission from ACS.

For further insight into these observations, femtosecond transient absorption (TA) measurements were performed. Optical excitation with a pump wavelength of 560 nm permitted selective excitation of only the bRsyn. The bleaching of the photoexcited supramolecular complex was monitored at 625 nm. FIG. 4 shows the lifetime decay trends of the excited natural bR and bRsyn supramolecular complexes with and without $TiO_2$ nanoparticles (25 µg/ml). For the artificial bRsyn membrane complex, the initial excited state decays with a time constant of 0.32±0.054 ps. It is notable, that this decay is faster than that of natural bR, where the latter has been previously demonstrated to exhibit a roughly 1.0 ps decay constant, ascribed to the chromophore isomerization. Not to be bound by theory, the origin of the threefold decrease in lifetime for bRsyn vs bR in natural PM suggests either an altered energy landscape for the photoisomerization, or another path of excited state deactivation such as electron transfer to some intermediate. Indeed, lipid environment, such as nature of lipid headgroup, length, flexibility of the hydrophobic chains that determined by linearity or branchiness as well as number of double bonds (e.g. branched isoprene chains in lipids from *Halobacterium* and 1,2-dimyristoyl-sn-glycero-3-phosphocholine, DMPC, in the nanodiscs particles), can remarkably alter dynamic processes in a transmembrane protein conformation and, therefore, function. Moreover, it was demonstrated that presence of the membrane scaffold protein 1E3D1 in the nanodiscs can affect lipid fluidity and therefore could also contribute to some variances in photoinduced process pathways with natural PMs and artificial bRsyn membrane architecture.

Differences of lateral dimensions of the nanoscale discs vs lengthy PM patches can result in some dissimilarities in measurements due to optical scattering. Not to be bound by theory, chemical structure differences between natural in wild PM patches from *Halobacterium* (branched isoprene chains) and artificial discrete discs particles (1,2-dimyristoyl-sn-glycero-3-phosphocholine, DMPC, and 1E3D1 scaffold protein) may mediate variations in the co-factor photoizomerization pathway and consequently in the photoexcited state deactivation.

The decay of bRsyn in the presence of $TiO_2$ becomes measurably faster with a lifetime of 0.19±0.02 ps, suggesting electron transfer with a rate of $\sim 2\times 10^{12}$/s to the nanoparticle acceptor. This rate is within a factor of 4 of the charge transfer rate that Applicants previously measured for bR-$TiO_2$ (also shown in FIG. 4). Efficiencies of CT for these complexes is difficult to ascertain from TA in this case however, owing to the dependence on interactions between the multiple components. While effects of the artificial membrane structure and composition on function of a transmembrane protein should be considered to ensure biological relevancy in model studies, synthetic cell-free produced complexes can successfully serve as a chassis for assembly with semiconductor materials to develop efficient photocatalytic systems.

In summary, Applicants report for the first time on deployment of a synthetic biology cell-free expression chassis for design and assembly of an entirely man-made energy transformation nano-bio hybrid. Similarly to a natural light-driven proton pump bR from the *Halobacterium salinarium*, the pump bRsyn in artificial purple membranes was integrated with $TiO_2$ semiconductor nanoparticles yielding a catalytic assembly for photon-to-hydrogen conversion. The system produces $H_2$ at a turnover rate of 240 µmol of $H_2$ (µmol protein)$^{-1}$ h$^{-1}$ under green and 17.74 mmol of $H_2$ (µmol protein)$^{-1}$ h$^{-1}$ under white light at ambient conditions, in water at neutral pH with methanol as a sacrificial electron donor.

While cell-free expression technique has been successfully developed as a handy approach for rapid high-fidelity production of membrane proteins for fundamental structure-functional studies, it also represents a certain practical interest for drug development for personalized medicines, for point-of-care fluidic protein expression and studies of viral infection. With current availability of time- and cost-efficient genes syntheses and further optimization of the cell-free expression schemes toward large-scale protein production and improved robustness of the biomimetic membranes technology, cell-free methodology can become a useful, flexible platform for on-demand expression of natural and designed light-responsive membrane architectures with precisely controllable structure, nanoscale dimensions, and photochemical properties. Such biological building blocks can consequently be integrated with semiconductor nanoparticles via systemic manipulation at nanoparticle-bio interface toward directed evolution of energy nanomaterials and nanosystems. Besides, this approach can be further translated into other higher complexity hierarchical artificial systems which span from biomimetic catalytic reactors and current generation toward metabolic pathways and signaling (e.g. neuronal, vision) networks.

REFERENCES

1 Lewis, N. S. Toward cost-effective solar energy use. *Science* 315, 798-801, doi:10.1126/science.1137014 (2007).
2 Lewis, N. S. Research opportunities to advance solar energy utilization. *Science* 351, 353-+, doi:10.1126/science.aad5117 (2016).
3 Maeda, K. et al. Photocatalyst releasing hydrogen from water—Enhancing catalytic performance holds promise for hydrogen production by water splitting in sunlight. *Nature* 440, 295-295, doi:10.1038/440295a (2006).

4 Yoon, T. P., Ischay, M. A. & Du, J. N. Visible light photocatalysis as a greener approach to photochemical synthesis. *Nat Chem* 2, 527-532, doi:10.1038/Nchem.687 (2010).

5 Utschig, L. M. et al. Photocatalytic Hydrogen Production from Noncovalent Biohybrid Photosystem I/Pt Nanoparticle Complexes. *J Phys Chem Lett* 2, 236-241, doi:10.1021/jz101728v (2011).

6 Bora, D. K. et al. Functionalization of Nanostructured Hematite Thin-Film Electrodes with the Light-Harvesting Membrane Protein C-Phycocyanin Yields an Enhanced Photocurrent. *Adv Funct Mater* 22, 490-502, doi:10.1002/adfm.201101830 (2012).

7 Schrantz, K. et al. Hematite photoanode co-functionalized with self-assembling melanin and C-phycocyanin for solar water splitting at neutral pH. *Catalysis Today* (2017).

8 Reisner, E., Powell, D. J., Cavazza, C., Fontecilla-Camps, J. C. & Armstrong, F. A. Visible Light-Driven H-2 Production by Hydrogenases Attached to Dye-Sensitized TiO2 Nanoparticles. *J Am Chem Soc* 131, 18457-18466, doi:10.1021/ja907923r (2009).

9 Balasubramanian, S., Wang, P., Schaller, R. D., Rajh, T. & Rozhkova, E. A. High-Performance Bioassisted Nanophotocatalyst for Hydrogen Production. *Nano Lett* 13, 3365-3371, doi:10.1021/nl4016655 (2013).

10 Wang, P. et al. Photoinduced Electron Transfer Pathways in Hydrogen-Evolving Reduced Graphene Oxide-Boosted Hybrid Nano-Bio Catalyst. *Acs Nano* 8, 7995-8002, doi:10.1021/nn502011p (2014).

11 Rozhkova, E. A. & Wang, P. in *Nanomaterials for Photocatalytic Chemistry* Vol. 12 *World Scientific Series in Nanoscience and Nanotechnology* (ed Y. Sun) 195-227 (2016).

12 Rusk, N. Advent of synthetic life. *Nat Methods* 7, 487-487, doi:10.1038/nmeth0710-487 (2010).

13 Rosenblum, G. & Cooperman, B. S. Engine out of the chassis: Cell-free protein synthesis and its uses. *Febs Lett* 588, 261-268, doi:10.1016/j.febslet.2013.10.016 (2014).

14 Gibson, D. G. et al. Creation of a Bacterial Cell Controlled by a Chemically Synthesized Genome. *Science* 329, 52-56, doi:10.1126/science.1190719 (2010).

15 Hodgman, C. E. & Jewett, M. C. Cell-free synthetic biology: Thinking outside the cell. *Metab Eng* 14, 261-269, doi:10.1016/j.ymben.2011.09.002 (2012).

16 Karim, A. S. & Jewett, M. C. A cell-free framework for rapid biosynthetic pathway prototyping and enzyme discovery. *Metab Eng* 36, 116-126, doi:10.1016/j.ymben.2016.03.002 (2016).

17 Sullivan, C. J. et al. A cell-free expression and purification process for rapid production of protein biologics. *Biotechnol J* 11, 238-248, doi:10.1002/biot.201500214 (2016).

18 Denisov, I. G. & Sligar, S. G. Nanodiscs for structural and functional studies of membrane proteins. *Nat Struct Mol Biol* 23, 481-486, doi:10.1038/nsmb.3195 (2016).

19 Bayburt, T. H., Grinkova, Y. V. & Sligar, S. G. Self-assembly of discoidal phospholipid bilayer nanoparticles with membrane scaffold proteins. *Nano Lett* 2, 853-856, doi:10.1021/nl025623k (2002).

20 Denisov, I. G., Grinkova, Y. V., Lazarides, A. A. & Sligar, S. G. Directed self-assembly of monodisperse phospholipid bilayer nanodiscs with controlled size. *J Am Chem Soc* 126, 3477-3487, doi:10.1021/ja0393574 (2004).

21 Lyukmanova, E. N. et al. Reconstituted high density lipoprotein particles: a promising medium for high-resolution NMR investigations of membrane proteins and membrane-active peptides. *Febs J* 275, 171-171 (2008).

22 Stepien, P., Polit, A. & Wisniewska-Becker, A. Comparative EPR studies on lipid bilayer properties in nanodiscs and liposomes. *Bba-Biomembranes* 1848, 60-66, doi:10.1016/j.bbamem.2014.10.004 (2015).

Shenkarev, Z. O. et al. Lipid-Protein Nanodiscs as Reference Medium in Detergent Screening for High-Resolution NMR Studies of Integral Membrane Proteins. *J Am Chem Soc* 132, 5628-+, doi:10.1021/ja9097498 (2010).

24 Dominik, P. K. et al. Conformational Chaperones for Structural Studies of Membrane Proteins Using Antibody Phage Display with Nanodiscs. *Structure* 24, 300-309, doi:10.1016/j.str.2015.11.014 (2016).

25 Dominik, P. K. & Kossiakoff, A. A. Phage display selections for affinity reagents to membrane proteins in nanodiscs. *Methods in enzymology* 557, 219-245, doi:10.1016/bs.mie.2014.12.032 (2015).

26 Timm, A. C., Shankles, P. G., Foster, C. M., Doktycz, M. J. & Retterer, S. T. Toward Microfluidic Reactors for Cell-Free Protein Synthesis at the Point-of-Care. *Small* 12, 810-817, doi:10.1002/smll.201502764 (2016).

27 Kuai, R., Ochyl, L. J., Bahjat, K. S., Schwendeman, A. & Moon, J. J. Designer vaccine nanodiscs for personalized cancer immunotherapy. *Nature Materials*, doi:DOI: 10.1038/NMAT4822 (2016).

28 Oesterhelt, D. & Stoeckenius, W. Rhodopsin-like protein from the purple membrane of *Halobacterium halobium*. *Nature: New biology* 233, 149-152 (1971).

29 Oesterhelt, D. & Stoeckenius, W. Functions of a new photoreceptor membrane. *Proc Natl Acad Sci USA* 70, 2853-2857 (1973).

30 Kuhlbrandt, W. Bacteriorhodopsin—the movie. *Nature* 406, 569-570, doi:10.1038/35020654 (2000).

31 Hampp, N. Bacteriorhodopsin as a photochromic retinal protein for optical memories. *Chem Rev* 100, 1755-1776, doi:Doi 10.1021/Cr980072x (2000).

32 Allam, N. K., Yen, C. W., Near, R. D. & El-Sayed, M. A. Bacteriorhodopsin/TiO2 nanotube arrays hybrid system for enhanced photoelectrochemical water splitting. *Energ Environ Sci* 4, 2909-2914, doi:10.1039/c1ee01447a (2011).

33 Zhao, Z., Wang, P., Xu, X., Sheves, M. & Jin, Y. Bacteriorhodopsin/Ag nanoparticle-based hybrid nano-bio electrocatalyst for efficient and robust H2 evolution from water. *J Am Chem Soc* 137, 2840-2843, doi:10.1021/jacs.5b00200 (2015).

34 Nassal, M., Mogi, T., Karnik, S. S. & Khorana, H. G. Structure-Function Studies on Bacteriorhodopsin 0.3. Total Synthesis of a Gene for Bacterioopsin and Its Expression in *Escherichia-Coli*. *J Biol Chem* 262, 9264-9270 (1987).

35 Nabiev, I. R., Efremov, R. G. & Chumanov, G. D. The Chromophore-Binding Site of Bacteriorhodopsin—Resonance Raman and Surface-Enhanced Resonance Raman-Spectroscopy and Quantum Chemical Study. *J Bioscience* 8, 363-374, doi:Doi 10.1007/Bf02703989 (1985).

36 Rakovich, A. et al. Resonance Energy Transfer Improves the Biological Function of Bacteriorhodopsin within a Hybrid Material Built from Purple Membranes and Semiconductor Quantum Dots. *Nano Lett* 10, 2640-2648, doi:10.1021/nl1013772 (2010).

37 Jin, Y. D., Friedman, N., Sheves, M., He, T. & Cahen, D. Bacteriorhodopsin (bR) as an electronic conduction medium: Current transport through bR-containing monolayers. *P Natl Acad Sci USA* 103, 8601-8606, doi:10.1073/pnas.0511234103 (2006).

38 Mathies, R. A., Cruz, C. H. B., Pollard, W. T. & Shank, C. V. Direct Observation of the Femtosecond Excited-State Cis-Trans Isomerization in Bacteriorhodopsin. *Science* 240, 777-779, doi:DOI 10.1126/science.3363359 (1988).

39 Herbst, J., Heyne, K. & Diller, R. Femtosecond infrared spectroscopy of bacteriorhodopsin chromophore isomerization. *Science* 297, 822-825, doi:DOI 10.1126/science.1072144 (2002).

40 Schenkl, S. et al. Insights into excited-state and isomerization dynamics of bacteriorhodopsin from ultrafast transient UV absorption. *P Natl Acad Sci USA* 103, 4101-4106, doi:10.1073/pnas.0506303103 (2006).

41 Van Eps, N., Caro, L. N., Morizumi, T. & Ernst, O. P. Characterizing rhodopsin signaling by EPR spectroscopy: from structure to dynamics. *Photoch Photobio Sci* 14, 1586-1597, doi:10.1039/c5pp00191a (2015).

42 Mahmoud L Nasr et al. Covalently circularized nanodiscs for studying membrane proteins and viral entry. *Nat Methods* 14, 49-52, doi:doi:10.1038/nmeth.4079.

43 Voloshin, A. & Swartz, J. in *Cell-free Protein Synthesis: Methods and Protocols* (eds A. Spirin & J. Swartz) Ch. 12, 207-236. (WILEY-VCH, 2008).

44 Jewett, M. C., Calhoun, K. A., Voloshin, A., Wuu, J. J. & Swartz, J. R. An integrated cell-free metabolic platform for protein production and synthetic biology. *Mol Syst Biol* 4, 220, doi:10.1038/msb.2008.57 (2008).

45 Voloshin, A. M. & Swartz, J. R. Efficient and scalable method for scaling up cell free protein synthesis in batch mode. *Biotechnol Bioeng* 91, 516-521, doi:10.1002/bit.20528 (2005).

46 A. Y. Shih, P. L. Freddolino, S. G. Sligar, K. Schulten, Disassembly of Nanodiscs with Cholate, *Nano Lett*, 7 (6), 1692-1696 (2007) tools.thermofisher.com/content/sfs/manuals/membranemaxproteinexpression_man.pdf 47 Ariga, K.; Li, J. B.; Fei, J. B.; Ji, Q. M.; Hill, J. P. Nanoarchitectonics for Dynamic Functional Materials from Atomic-/Molecular-Level Manipulation to Macroscopic Action. *Adv Mater* 2016, 28, 1251-1286.

48 Aono, M.; Ariga, K. The Way to Nanoarchitectonics and the Way of Nanoarchitectonics. *Adv Mater* 2016, 28, 989-992.

49 Wagner, N. L.; Greco, J. A.; Ranaghan, M. J.; Birge, R. R. Directed Evolution of Bacteriorhodopsin for Applications in Bioelectronics. *J R Soc Interface* 2013, 10, 20130197.

50 Roy, P.; Kantor-Uriel, N.; Mishra, D.; Dutta, S.; Friedman, N.; Sheves, M.; Naaman, R. Spin-Controlled Photoluminescence in Hybrid Nanoparticles Purple Membrane System. *ACS Nano* 2016, 10, 4525-4531.

51 Johnson, P. J. M.; Halpin, A.; Morizumi, T.; Brown, L. S.; Prokhorenko, V. I.; Ernst, O. P.; Miller, R. J. D. The Photocycle and Ultrafast Vibrational Dynamics of Bacteriorhodopsin in Lipid Nanodiscs. *Phys Chem Chem Phys* 2014, 16, 21310-21320.

52 Mori, T.; Sakakibara, K.; Endo, H.; Akada, M.; Okamoto, K.; Shundo, A.; Lee, M. V.; Ji, Q. M.; Fujisawa, T.; Oka, K.; Matsumoto, M.; Sakai, H.; Abe, M.; Hill, J. P.; Ariga, K. Langmuir Nanoarchitectonics: One-Touch Fabrication of Regularly Sized Nanodisks at the Air-Water Interface. *Langmuir* 2013, 29, 7239-7248.

What is claimed is:

1. A photocatalyst comprising a synthetically produced opsin disposed in an artificial purple membrane non-covalently coupled to a semiconductor nanocluster.

2. The photocatalyst of claim 1, wherein the synthetically produced opsin is produced in a cell-free system.

3. The photocatalyst of claim 1, wherein the synthetically produced opsin is a rhodopsin capable of the light-driven translocation of ions across the artificial purple membrane.

4. The photocatalyst of claim 3, wherein the synthetically produced opsin is bacteriorhodopsin.

5. The photocatalyst of claim 1, wherein the semiconductor is selected from the group of: Si, SiC, GaAs, GaInP, GaN, CdS, CdSe, $TiO_2$, $VO_2$, $ZrO_2$, $Fe_3O_4$, $Fe_2O_3$, $MnO_2$, NiO, ZnO, $Bi_2O_3$ and CuO.

6. The photocatalyst of claim 5, wherein the semiconductor is $TiO_2$.

7. The photocatalyst of claim 1, further comprising a co-catalyst.

8. The photocatalyst of claim 7, wherein the co-catalyst is selected from the group of: Pt, Pd, Au, Ag, and composites of thereof.

9. The photocatalyst of claim 8, wherein the co-catalyst is Pt.

10. The photocatalyst of claim 7, wherein the co-catalyst is dotted on the semiconductor nanocluster.

11. The photocatalyst of claim 1, wherein the photocatalyst is active in white light and neutral pH.

12. A fuel cell comprising:
a photocatalyst comprising a synthetically produced opsin disposed in an artificial purple membrane non-covalently coupled to a semiconductor nanocluster.

13. The fuel cell of claim 12, wherein the photocatalyst is provided in an aqueous slurry.

14. A method of producing hydrogen, comprising photocatalytically splitting water using the photocatalyst of claim 1.

15. The photocatalyst of claim 1, wherein the semiconductor is a metal oxide.

* * * * *